US010495557B2

(12) United States Patent
Tsujii et al.

(10) Patent No.: US 10,495,557 B2
(45) Date of Patent: Dec. 3, 2019

(54) HARDNESS TESTER AND HARDNESS TESTING METHOD

(71) Applicant: MITUTOYO CORPORATION, Kanagawa (JP)

(72) Inventors: Masaharu Tsujii, Kanagawa (JP); Satoko Mori, Kanagawa (JP); Takayuki Yamada, Kanagawa (JP)

(73) Assignee: MITUTOYO CORPORATION, Kanagawa (JP)

( * ) Notice: Subject to any disclaimer, the term of this patent is extended or adjusted under 35 U.S.C. 154(b) by 24 days.

(21) Appl. No.: 15/869,384

(22) Filed: Jan. 12, 2018

(65) Prior Publication Data

US 2018/0217040 A1  Aug. 2, 2018

(30) Foreign Application Priority Data

Jan. 27, 2017 (JP) .................................. 2017-012750

(51) Int. Cl.
*G01N 3/42* (2006.01)
*G01N 3/62* (2006.01)

(52) U.S. Cl.
CPC .............. *G01N 3/42* (2013.01); *G01N 3/62* (2013.01); *G01N 2203/0082* (2013.01); *G01N 2203/0208* (2013.01); *G01N 2203/0605* (2013.01); *G01N 2203/0676* (2013.01)

(58) Field of Classification Search
CPC ....................................................... G01N 3/42
See application file for complete search history.

(56) References Cited

U.S. PATENT DOCUMENTS

| 8,087,282 | B2 | 1/2012 | Sawa et al. |
| 9,291,538 | B2 | 3/2016 | Sawa |
| 9,341,554 | B2 | 5/2016 | Tsujii et al. |
| 2017/0102305 | A1 | 4/2017 | Tsujii et al. |
| 2017/0122856 | A1 | 5/2017 | Koshimizu |

FOREIGN PATENT DOCUMENTS

| JP | 4942579 B2 | 5/2012 |
| JP | 2013-019862 A | 1/2013 |

*Primary Examiner* — Lisa M Caputo
*Assistant Examiner* — Alex T Devito
(74) *Attorney, Agent, or Firm* — Greenblum & Bernstein, P.L.C.

(57) ABSTRACT

A hardness tester includes a measurer (CPU) measuring a value for a material characteristic of a sample in conjunction with formation of an indentation, an acquirer (CPU) acquiring measurement data associated with the value for the material characteristic of the sample measured by the measurer, and a determiner (CPU) accumulating a predetermined value for the material characteristic based on the measurement data acquired by the acquirer and determining a time to replace the indenter based on the accumulated value for the material characteristic.

9 Claims, 7 Drawing Sheets

HARDNESS TESTER AND HARDNESS TESTING METHOD

CROSS-REFERENCE TO RELATED APPLICATIONS

The present application claims priority under 35 U.S.C. § 119 of Japanese Application No. 2017-012750, filed on Jan. 27, 2017, the disclosure of which is expressly incorporated by reference herein in its entirety.

BACKGROUND OF THE INVENTION

1. Field of the Invention

The present invention relates to a hardness tester and to a hardness testing method.

2. Description of Related Art

Conventionally, a material tester is known in which a hardness tester forms an indentation by pressing an indenter column into a surface of a sample, the indenter column having an indenter on a foremost end thereof. Then, using a displacement gauge, the hardness tester measures a depth of indentation (displacement amount of the indenter) at the time the indentation is formed. Using a relationship between the measured displacement amount and a test force loaded on the indenter, the hardness tester measures a value for a material characteristic of the sample, such as hardness (see, for example, Japanese Patent Laid-open Publication No. 2013-019862, and Japanese Patent No. 4942579). In a material testing method (instrumented indentation test) such as nanoindentation evaluating the depth of indentation of the indenter using the above-described hardness tester, the value for the material characteristic is calculated by dynamically measuring the depth to which the indenter is pressed into the sample. Therefore, monitoring a tip shape of the indenter is important so as not to adversely affect the calculated result due to a change in the tip shape of the indenter caused by abrasion and the like.

In the conventional technology mentioned above, the number of tests was recorded on a system which controls the hardness tester and a time to replace the indenter was left entirely to a user's judgment. For example, when the recorded number of tests exceeds a predetermined set value, a determination is made that the indenter needs to be replaced. When the test is then performed with a hardness reference piece and a change (increase) in a hardness value is confirmed, the indenter is replaced. However, in the conventional technology, the user needs to determine when the indenter is to be replaced, thereby causing excessive effort. In addition, because there is a risk that each user may make a different judgment, accurately determining the time to replace the indenter is difficult.

SUMMARY OF THE INVENTION

The present invention provides a hardness tester and a hardness testing method that enable greater accuracy in determining a time to replace an indenter and enable remarkably enhanced maintainability.

To achieve the above, according to one aspect of the present invention, a hardness tester loads a predetermined test force on an indenter and forms an indentation by pressing the indenter into a surface of a sample. The hardness tester includes a measurer measuring a value for a material characteristic of the sample in conjunction with formation of an indentation; an acquirer acquiring measurement data associated with the value for the material characteristic of the sample measured by the measurer; and a determiner accumulating a predetermined value for the material characteristic based on the measurement data acquired by the acquirer and determining the time to replace the indenter based on the accumulated value for the material characteristic.

In the hardness tester according to another aspect of the present invention, the measurer measures a depth of indentation at the time the indentation is formed, and measures the value for the material characteristic of the sample using a relationship between the depth of indentation and a test force loaded on the indenter. The determiner calculates a mechanical workload generated during indentation based on the measurement data, accumulates the calculated mechanical workload for each hardness value, and determines the time to replace the indenter based on the accumulated mechanical workload for each hardness value.

The hardness tester according to another aspect of the present invention is provided with a display controller causing a display to display a warning to prompt replacement of the indenter when replacement of the indenter is determined to be necessary.

In the hardness tester according to another aspect of the present invention, when a number of tests (number of times the value for the material characteristic of the sample is measured) exceeds a set value, the determiner determines that the indenter needs to be replaced; and when the number of tests does not exceed the set value, the determiner determines the time to replace the indenter based on the measurement data acquired by the acquirer.

Another aspect of the present invention is a hardness testing method of the hardness tester which loads the predetermined test force on the indenter and forms the indentation by pressing the indenter into the surface of the sample. The hardness testing method includes a measuring process measuring the value for the material characteristic of the sample in conjunction with the formation of the indentation; an acquiring process acquiring measurement data associated with the value for the material characteristic of the sample measured in the measuring process; and a determining process determining the time to replace the indenter based on the measurement data acquired in the acquiring process.

With the present invention, the time to replace the indenter can be determined more accurately and maintainability can be remarkably enhanced.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF THE INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the forms of the present invention may be embodied in practice.

Hereafter, an embodiment of the present invention is described with reference to the drawings.

1. Description of Configuration

Figure 1:
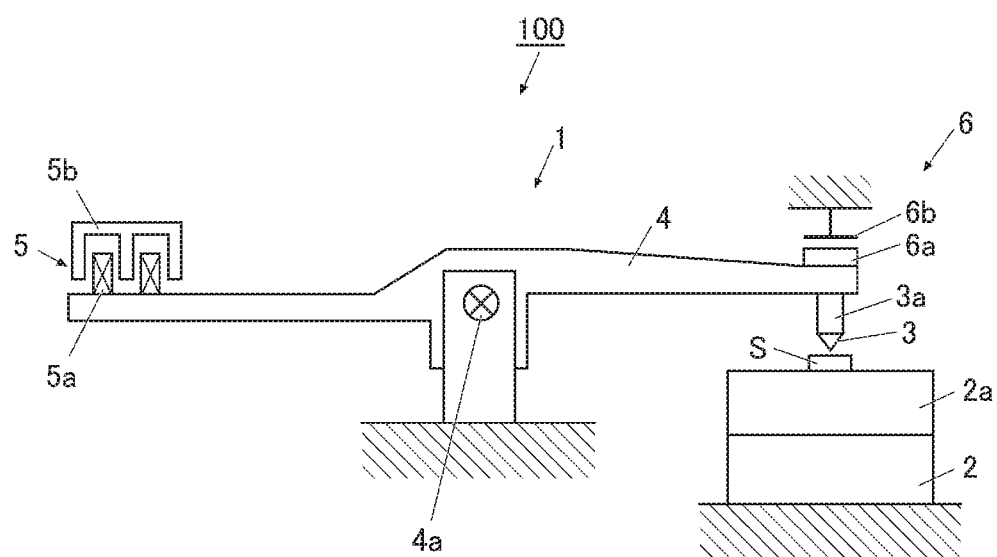
FIG. 1 is a side view illustrating an overall configuration of a hardness tester according to the present invention.
Figure 2:
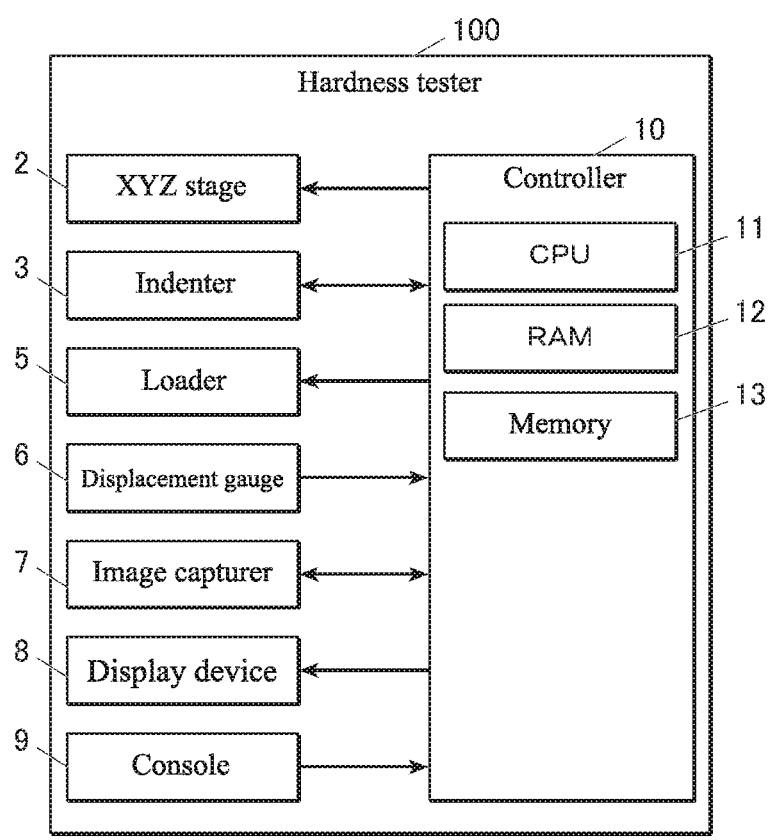
FIG. 2 is a block diagram illustrating a control structure of the hardness tester according to the present invention.

A hardness tester 100 according to the present embodiment is an instrumented indentation tester capable of continuously monitoring a load (test force) placed on an indenter 3 and a displacement amount (indentation depth) of the indenter 3. As shown in FIGS. 1 and 2, the hardness tester 100 includes a tester main body 1 to which each component is provided and a controller 10 performing all-inclusive control of the tester main body 1.

The tester main body 1 includes, as an indentation formation mechanism, an XYZ stage 2 displacing a sample S in X, Y, and Z directions; a loading lever 4 having at one end thereof an indenter 3, which forms an indentation in the sample S; a loader 5 placing a predetermined load on the loading lever 4; a displacement gauge 6 detecting a displacement amount of the indenter 3; an image capturer 7 capturing an image of at least the indentation formed on a surface of the sample S; a display device 8; and a console 9.

The XYZ stage 2 is configured to displace in the X, Y, and Z directions (i.e., in horizontal and vertical directions) according to a control signal input from the controller 10. The sample S is displaced forward/backward, to the left/right, and upward/downward by the XYZ stage 2 so as to adjust a position of the sample S with respect to the indenter 3. In addition, the XYZ stage 2 holds the sample S with a sample holding stage 2a such that the sample S resting on an upper surface thereof does not shift during test measurement.

Examples of the sample S include DLC, silicon rubber, and natural rubber. Specifically, the hardness tester 100 according to the present embodiment can measure thin films such as vapor-deposited film and semiconductor materials; surface treatment layers; various kinds of plastics; various kinds of rubber; fragile materials such as micro-filaments, glass, and ceramics; microelectronics; and the like.

The indenter 3 is provided so as to be vertically displaceable above the XYZ stage 2, on which the sample S is placed. A predetermined load is provided to the indenter 3 and a bottom end (tip) of an indenter main body 31 is pressed vertically into a top surface (test surface) of the sample S, thus forming the indentation in the top surface of the sample S.

Figure 3A:
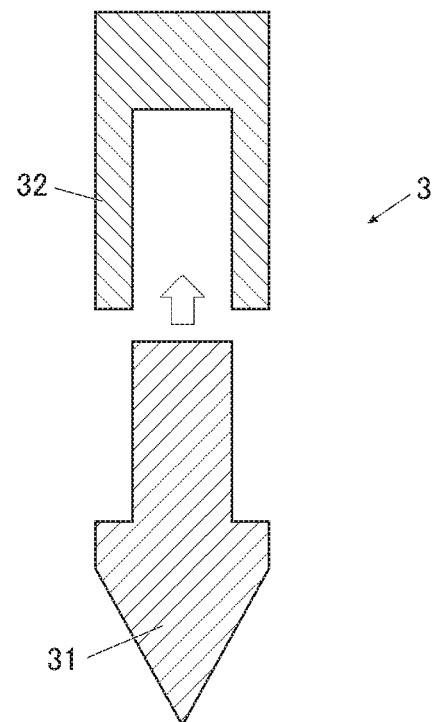
FIGS. 3A and 3B are cross-sectional views of an indenter as viewed from one side.
Figure 3B:
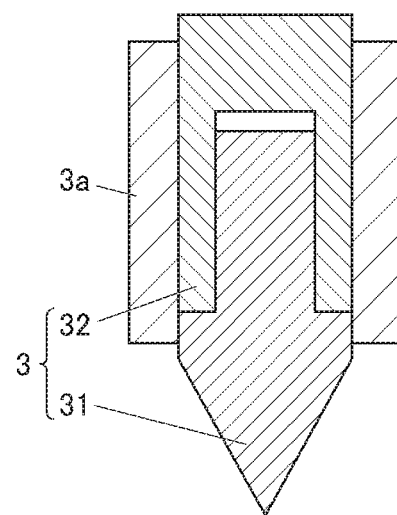

As shown in FIGS. 3A and 3B, the indenter 3 is configured with the indenter main body 31, which is pressed into the sample S from the tip; and a holder 32 into which the indenter main body 31 is pressed, and which holds the indenter main body 31.

The tip of the indenter main body 31 is formed in a shape prescribed by any of various indenters such as a Vickers, Berkovich, Rockwell, Knoop, or Brinell indenter. In the present embodiment, a Berkovich indenter is used as the indenter main body 31. The Berkovich indenter is a three-sided pyramid diamond indenter. The Berkovich indenter has a face angle of 65.03° with respect to an indenter center axis and has the same indenter surface area ratio as the Vickers indenter with respect to the direction of indentation depth. With the three-sided pyramid, concentrating the tip at one point is easier (in other words, the tip is more easily sharpened) as compared to a four-sided pyramid. The hardness tester 100 according to the present embodiment is a tester measuring a minute depth of indentation, and a slight difference in the shape of the indenter tip greatly affects the test result. Therefore, in the present embodiment, the Berkovich indenter (three-sided pyramid indenter) is used. Such an indenter main body 31 is detachably held by the holder 32 by pressing the rear end portion (top end portion) of the indenter main body 31 into the holder 32. Because the indenter main body 31 is detachable with respect to the holder 32, it is possible to replace only the indenter main body 31 in cases where, for example, the tip of the indenter main body 31 becomes worn or damaged.

The holder 32 is a cylindrical member having an interior space capable of accommodating the rear end portion of the indenter main body 31. The rear end of the indenter main body 31 is pressed in through the bottom end of the holder 32. In a state where the indenter main body 31 is held by the holder 32, the top end portion of the holder 32 is detachably fixated to an indenter shaft 3a by a screw, for example.

The loading lever 4 is formed to be substantially pole-shaped. The loading lever 4 is rotatably fixated at an approximately central portion thereof atop a stand via a cross spring 4a. The indenter 3 is provided at a first end of the loading lever 4 so as to freely contact and separate from the sample S from above, the sample S resting atop the sample holding stage 2a. The indenter 3 presses against the surface of the sample S to form the indentation therein. In addition, at a second end of the loading lever 4, a force coil 5a is provided that configures the loader 5.

The loader 5 is a force motor and includes the force coil 5a attached to the loading lever 4 and a fixed magnet 5b fixed so as to oppose the force coil 5a. The loader 5 employs a driving force to rotate the loading lever 4 according to a control signal input from the controller 10. The driving force is a force generated by electromagnetic induction between a magnetic field created in a gap by the fixed magnet 5b and an electric current flowing in the force coil 5a, which is positioned inside the gap. By rotating the loading lever 4, the end of the loading lever 4 on the indenter 3 side is displaced downward and the indenter 3 is pressed into the sample S.

The displacement gauge 6 is an electrostatic capacitance-type displacement sensor and is configured with a movable polar plate 6a provided to the end of the loading lever 4 on the indenter 3 side and a fixed polar plate 6b fixed in place so as to oppose the movable polar plate 6a. The displacement gauge 6 detects a variation in electrostatic capacitance between the movable polar plate 6a and the fixed polar plate 6b, and thereby detects the displacement amount when the indenter 3 forms the indentation in the sample S (indentation depth when the indenter 3 is pressed into the sample S). A displacement signal based on the detected displacement amount is then output to the controller 10. Moreover, the electrostatic capacitance-type displacement sensor is offered as an exemplary displacement gauge 6; however, the displacement gauge 6 is not limited to this and may, for example, be an optical-type displacement sensor or an eddy current-type displacement sensor.

The image capturer 7 is configured with a camera, for example, and captures an image of the indentation formed on the surface of the sample S by the indenter 3 atop the sample holding stage 2a, for example, according to a control signal input from the controller 10.

The display device 8 is, for example, a liquid crystal display panel and performs a process of displaying the image of the surface of the sample S captured by the image capturer 7, various kinds of test results, and the like according to a control signal input from the controller 10.

The console 9 is, for example, a group of operation keys such as in a keyboard and, when the console 9 receives the operations from the user, the console 9 outputs an operation signal associated with that operation to the controller 10. Moreover, the console 9 may also include a pointing device such as a mouse or a touch screen, a remote control, and other operation devices. The console 9 is operated when the user provides an instruction input to perform hardness testing on the sample S, defines the test force (i.e., the load) placed on the indenter 3, and the like.

The controller 10 includes a CPU 11, a RAM 12, and a memory 13. Through a system bus or the like, the controller 10 is connected to the XYZ stage 2, the indenter 3, the loader 5, the displacement gauge 6, the image capturer 7, the display device 8, and the console 9, for example.

The CPU 11 performs various control processes according to various processing programs for use in the hardness tester that are stored in the memory 13. The RAM 12 includes a program storage region for extracting the processing programs executed by the CPU 11 and a data storage region storing input data, processing results generated when the processing programs are executed, or the like. The memory 13 stores a system program executable by the hardness tester 100; various kinds of processing programs executable by the system program; data to be used when the various kinds of processing programs are executed; and data on results of the various processes calculated by the CPU 11. Moreover, each program is stored in the memory 13 in the form of a programming code that is readable by the computer.

Figure 4:
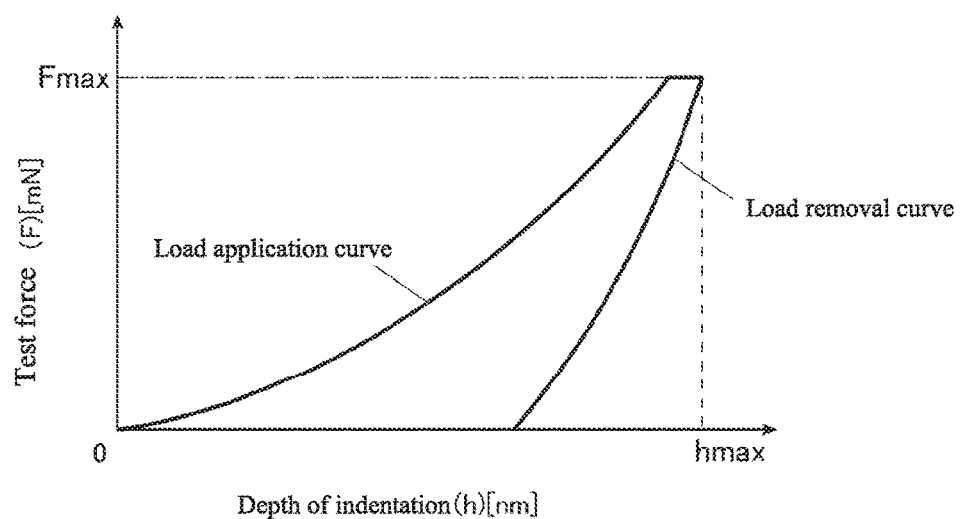
FIG. 4 illustrates an exemplary pressing curve.

For example, when the user provides an instruction input to the console 9 to perform hardness testing on the sample S, the CPU 11 provides a predetermined load to the indenter 3, presses the indenter 3 into the surface of the sample S to form an indentation, and measures a pressing curve composed of the detected displacement amount of the indenter 3 (indentation depth (h)) and the detected test force (F) loaded on the indenter 3 during formation of the indentation (instrumented indentation test). As shown in FIG. 4, during formation of the indentation, the pressing curve is obtained by gradually increasing a load applied to the indenter 3 until reaching a defined maximum test force (Fmax) (load application process) and a load application curve is measured in that process; and also, by gradually decreasing the load applied to the indenter 3 (load removal process) after the load applied to the indenter 3 reaches the maximum test force and a load removal curve is measured in that process.

2. Description of Operations

Figure 5:
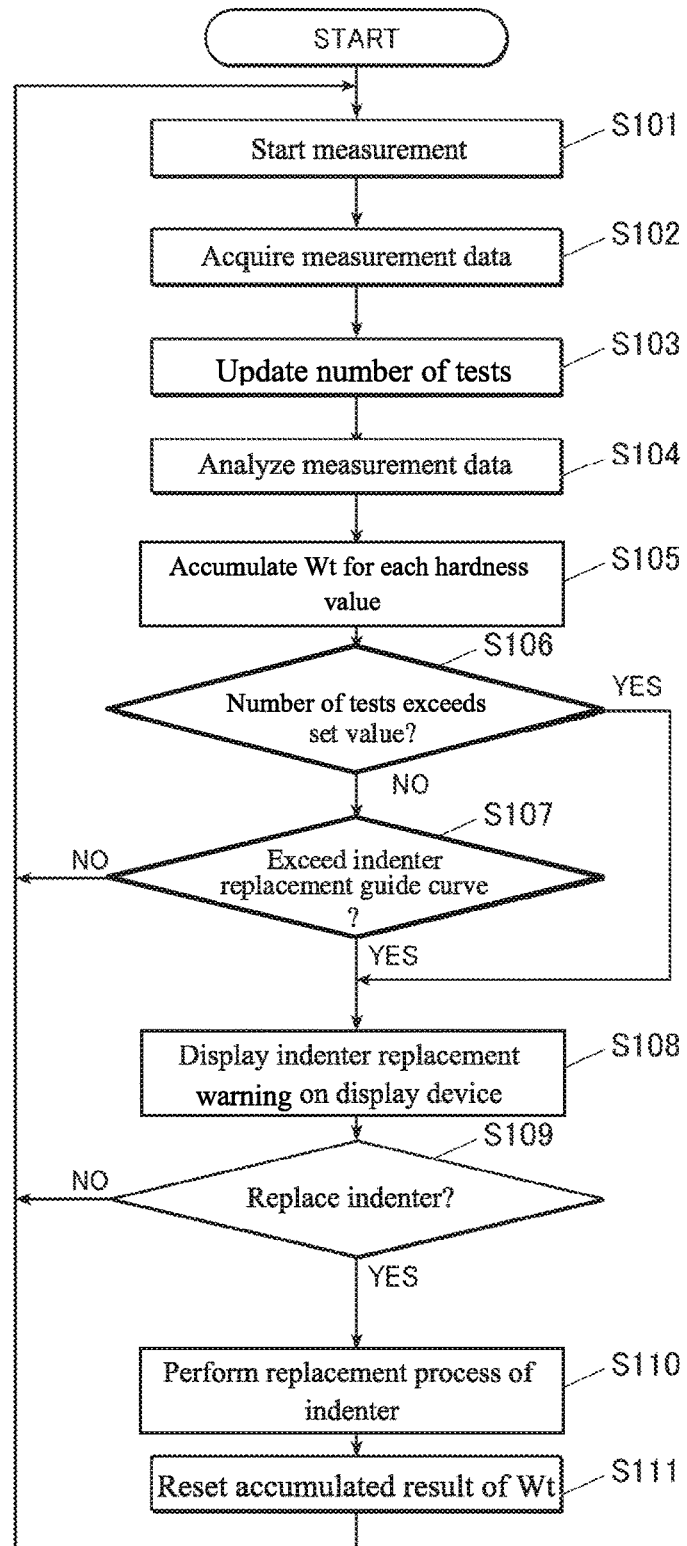
FIG. 5 is a flow chart illustrating operations of the hardness tester according to an embodiment.

Next, operations of the hardness tester 100 according to the present embodiment are described with reference to the flow chart of FIG. 5. In FIG. 5, an example is described in which a sample S having uniform hardness on the surface and inside of the sample S (that is, the surface is not hardened) is measured.

First, the CPU 11 of the controller 10 starts measurement of a value for a material characteristic of the sample S, such as hardness (step S101: measurement process). In the present embodiment, the CPU 11 starts the instrumented indentation test that provides the predetermined load to the indenter 3 and presses the indenter 3 into the surface of the sample S to form the indentation; and that measures a pressing curve composed of the detected displacement amount of the indenter 3 (indentation depth (h)) and the detected test force (F) loaded on the indenter 3 during formation of the indentation. In other words, the CPU 11 serves as a measurer in the present invention.

Next, the CPU 11 acquires measurement data associated with the values for the material characteristics of the sample S for which measurement is started in step S101 (step S102: acquiring process). Specifically, the CPU 11 acquires the pressing curve illustrated in FIG. 4. In other words, the CPU 11 serves as an acquirer in the present invention. Then, the CPU 11 updates the number of hardness tests (instrumented indentation tests) performed (step S103). Specifically, the CPU 11 adds one to the number of hardness tests. The number of hardness tests is stored in the memory 13, for example.

Figure 6:
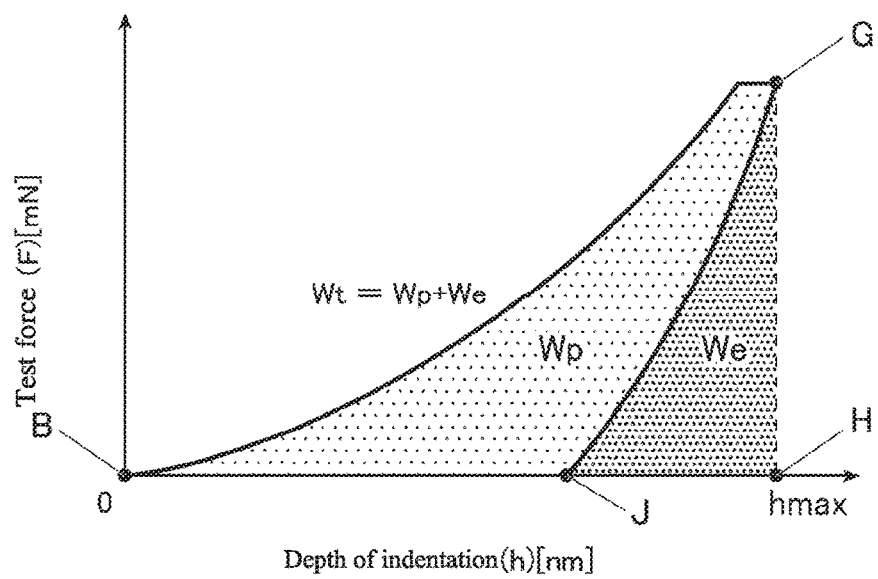
FIG. 6 illustrates an exemplary method of calculating a mechanical workload generated during indentation.

Next, the CPU 11 analyzes the measurement data acquired in step S102 (step S104). For example, the CPU 11 calculates a mechanical workload Wt generated during the indentation based on the pressing curve. The mechanical workload Wt generated during the indentation is the sum of an indentation workload We caused by elastic deformation and an indentation workload Wp caused by plastic deformation (Wt=We+Wp). Wp is an area surrounded by a curved line that passes through points B, G, and J in FIG. 6. We is an area surrounded by a point H and a curved line that passes through points J and G. Accordingly, Wt is an area surrounded by the point H and a curved line that passes through the points B and G.

Figure 7:
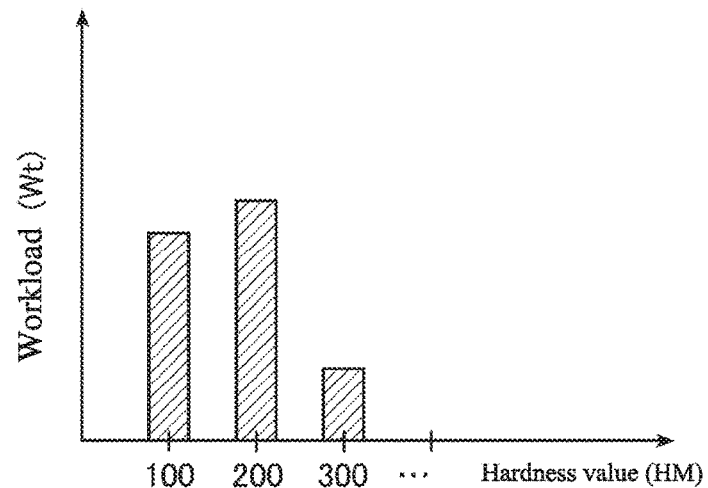
FIG. 7 illustrates exemplary mechanical workloads accumulated for each measured hardness value.

Next, for each measured hardness value, the CPU 11 accumulates the mechanical workload Wt generated during the indentation (step S105). In this example, the mechanical workload Wt generated during the indentation changes according to the test force or the hardness of the sample S. For example, when the hardness of the samples S is the same, the mechanical workload Wt generated during the indentation is proportional to the test force. However, when the samples S have different hardnesses, the softer the sample S is, the greater the depth of the indentation is, and therefore, the mechanical workload Wt generated during the indentation becomes a large value. Therefore, the mechanical workload Wt generated during the indentation must be monitored as an accumulation for respective hardness value. Monitoring the mechanical workload Wt generated during the indentation for each hardness value in this way enables confirmation of how the indenter 3 is used. FIG. 7 illustrates exemplary mechanical workloads Wt accumulated for each measured hardness value HM. In the example shown in FIG. 7, compared with a case when the hardness value HM is 100, the accumulated mechanical workload Wt is greater when the hardness value HM is 200, and the accumulated mechanical workload Wt is smaller when the hardness value HM is 300.

Next, the CPU 11 determines whether or not the number of tests exceeds the set value (step S106). The set value can be set as appropriate by the user, however, the set time is preferably set to a time when wear on the indenter 3 is notable and hinders the measurement. When the number of tests is determined to exceed the set value (step S106: YES), the CPU 11 determines that the indenter 3 needs to be replaced and the CPU 11 proceeds to step S108. On the other hand, when the number of tests is determined not to exceed the set value (that is, the number of tests is at or below the set value) (step S106: NO), the CPU 11 determines that a full examination of whether or not the indenter 3 requires replacement is necessary, and the CPU 11 proceeds to the next step, S107.

Figure 8:
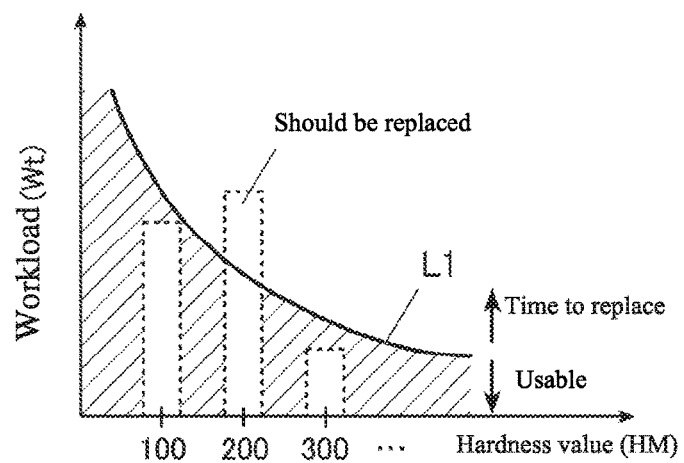
FIG. 8 illustrates an exemplary indenter replacement guide curve.

Then, the CPU 11 determines whether the accumulated mechanical workload Wt for each hardness value HM in step S105 exceeds the guide curve (indenter replacement guide curve) indicating the time to replace the indenter 3 (step S107: determining process). Specifically, when the accumulated mechanical workload Wt exceeds the indenter replacement guide curve for at least one hardness value HM in the accumulated mechanical workload Wt for each hardness value HM, the CPU 11 determines that the mechanical workload Wt exceeds the indenter replacement guide curve. In other words, the CPU 11 serves as a determiner in the present invention. FIG. 8 illustrates an exemplary indenter replacement guide curve. FIG. 8 illustrates an example where, when the hardness value HM is 200, the accumulated mechanical workload Wt exceeds an indenter replacement guide curve L1. When the accumulated mechanical workload Wt is determined to exceed the indenter replacement guide curve L1 (step S107: YES), the CPU 11 determines that the indenter 3 needs to be replaced and the CPU 11 proceeds to the next step, S108. On the other hand, when the accumulated mechanical workload Wt is determined not to exceed the indenter replacement guide curve L1 (that is, is determined to be at or below the indenter replacement guide curve L1) (step S107: NO), the CPU 11 determines that the indenter 3 does not need to be replaced and the CPU 11 proceeds to step S101 to start the measurement of the value for the material characteristic again.

Next, the CPU 11 displays on the display device 8 a warning to prompt the replacement of the indenter 3 (indenter replacement warning) (step S108). At this point in time, the CPU 11 also displays a screen (such as buttons) for the user to select whether or not to perform the replacement of the indenter 3.

Next, the CPU 11 determines whether or not the indenter 3 is to be replaced (step S109). Specifically, when an operation (such as pressing the replacement button) instructing that the indenter 3 be replaced is received from the user in the display screen of the indenter replacement warning displayed on the display device 8 (step S108), the CPU 11 determines that the indenter 3 is to be replaced. In other words, the CPU 11 serves as a display controller in the present invention. In a case where the CPU 11 determines that the indenter 3 is to be replaced (step S109: YES), the CPU 11 proceeds to the next step, S110. On the other hand, when the CPU 11 determines that the replacement of the indenter 3 is not to be performed (step S109: NO), the CPU 11 proceeds to step S101 to start the measurement of the value for the material characteristic again.

Next, the CPU 11 performs a process to replace the indenter 3 (indenter replacement process) (step S110). The indenter replacement process includes, in addition to the process to replace the indenter, for example, a process to correct the weight of the hardness tester 100 and the like. Moreover, the indenter 3 may be replaced automatically, or may be manually replaced by the user.

Next, the CPU 11 resets the accumulated result of the mechanical workload Wt generated during the indentation (step S111). In other words, with the replacement of the indenter 3, the CPU 11 resets the accumulated result because the accumulated mechanical workload Wt of the indenter 3 prior to the replacement has no meaning. After that, the CPU 11 proceeds to step S101 and starts the measurement of the value for the material characteristic again.

3. Effect

As mentioned above, the hardness tester 100 according to the present embodiment includes a measurer (CPU 11) measuring the value for the material characteristic of the sample S in conjunction with formation of the indentation, an acquirer (CPU 11) acquiring the measurement data associated with the value for the material characteristic of the sample S measured by the measurer, and a determiner (CPU 11) accumulating the predetermined value for the material characteristic (mechanical workload in the present embodiment) based on the measurement data acquired by the acquirer and determining the time to replace the indenter 3 based on the accumulated value for the material characteristic. Therefore, in the hardness tester 100 according to the present embodiment, monitoring the value for the material characteristic of the measured sample S enables confirmation of how the indenter 3 is used, which enables the time to replace the indenter 3 to be determined more accurately and enables remarkably enhanced maintainability.

Particularly, in the hardness tester 100 according to the present embodiment, the measurer measures the depth of indentation during formation of the indentation, and measures the value for the material characteristic of the sample S using the relationship between the depth of indentation and the test force loaded on the indenter 3. The determiner calculates the mechanical workload generated during the indentation based on the measurement data, accumulates the calculated mechanical workload for each hardness value, and determines the time to replace the indenter 3 based on the accumulated mechanical workload for each hardness value. Therefore, in the hardness tester 100 according to the present embodiment, monitoring the mechanical workload Wt generated during the indentation for each hardness value enables confirmation of how the indenter 3 is used, which enables the time to replace the indenter 3 to be determined more accurately and enables remarkably enhanced maintainability.

In addition, the hardness tester 100 according to the present embodiment includes the display controller (CPU 11) to allow displaying the warning to prompt the replacement of the indenter 3 on a display (the display device 8) when the determiner determines that the indenter 3 needs to be replaced. Therefore, in the hardness tester 100 according to the present embodiment, the warning to prompt the replacement of the indenter 3 can be transmitted to the user. Thus, the final determination as to whether or not to replace the indenter 3 can be entrusted to the user, thereby achieving flexible operation that is responsive to the circumstances of the user's usage.

In addition, in the hardness tester 100 according to the present embodiment, when the number of tests (number of times the value for the material characteristic of the sample S is measured) exceeds the set value, the determiner determines that the indenter 3 needs to be replaced; and when the number of tests does not exceed the set value, the determiner determines the time to replace the indenter 3 based on the measurement data acquired by the acquirer. In this example, the set value can be set to a time when wear on the indenter 3 is notable and hinders the measurement. Therefore, the hardness tester 100 according to the present embodiment can omit a complicated determination that uses the indenter replacement guide curve L1 when a determination can be made, based on the number of tests, that the possibility of replacing the indenter 3 is high, and therefore, the process can be simplified and accelerated.

In the above, a concrete description is given based on an embodiment according to the present invention. However, the present invention is not limited to the above-described embodiment and can be modified without deviating from the scope of the invention.

For example, in the above-described embodiment, a description is given in which the mechanical workload Wt serves as an example of the value for the material characteristic used when determining the time to replace the indenter 3; however, the present embodiment is not limited to this. For example, instead of the mechanical workload Wt, a value for another material characteristic such as the hardness value of the sample S, Young's modulus, or the like may be used. In addition, by appropriately combining the mechanical workload Wt, the hardness value of the sample S, Young's modulus, or the like, the value may be used as an index when determining the time for replacement. In this case, in view of a degree of priority assigned to various values for the material characteristics, each of the values for the material characteristics may be multiplied by a coefficient so as to strengthen the influence of the higher priority characteristics.

In addition, in the above-described embodiment, an instrumented indentation tester is described to exemplify the hardness tester 100. However, the present invention is not limited to this. For example, in a case where the hardness value of the sample S is used as the measurement data used when determining the time to replace the indenter 3, other hardness testers such as a Vickers hardness tester, Knoop hardness tester, Brinell hardness tester, and the like may be applied in place of the instrumented indentation tester.

In addition, in the above-described embodiment, when replacement of the indenter 3 is determined to be necessary, the warning to prompt the replacement of the indenter 3 is displayed on the display device 8 in step S108 of FIG. 5. However, the present invention is not limited to this. For example, instead of performing a display of the warning to prompt the replacement of the indenter 3 on the display device 8, by providing a speaker and the like which is capable of outputting audio, the warning may be output as audio from the speaker. Alternatively, audio may be output from the speaker simultaneously with performing the display on the display device 8.

In addition, in the above-described embodiment, when the number of times the value for the material characteristic of the sample S is measured (number of tests) exceeds the set value in step S106 of FIG. 5, replacement of the indenter 3 is determined to be necessary. However, the present invention is not limited to this. For example, the process of step S107 (process to determine the time to replace the indenter 3 using the indenter replacement guide curve L1 (see FIG. 8)) may be performed all the time, without performing the step S106 and regardless of the number of tests.

In addition, within a scope not deviating from the substance of the present invention, appropriate modifications may also be made to detailed structures and operations of each component configuring the hardness tester.

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular structures, materials and embodiments, the present invention is not intended to be limited to the particulars disclosed herein; rather, the present invention extends to all functionally equivalent structures, methods and uses, such as are within the scope of the appended claims.

The present invention is not limited to the above described embodiments, and various variations and modifications may be possible without departing from the scope of the present invention.

What is claimed is:

1. A hardness tester for loading a predetermined test force on an indenter and forming an indentation by pressing the indenter into a surface of a sample, the hardness tester comprising a processor and a memory that stores an instruction, the hardness tester further comprising, as a configuration when the processor executes the instruction stored in the memory:
   a measurer that measures a value for a material characteristic of the sample in conjunction with formation of an indentation;
   an acquirer that acquires measurement data associated with the value for the material characteristic of the sample measured by the measurer; and
   a determiner that accumulates a value for the material characteristic based on the measurement data acquired by the acquirer and determining a time to replace the indenter based on the accumulated value for the material characteristic.

2. The hardness tester according to claim 1, wherein:
the measurer further measures:
   a depth of indentation at the time the indentation is formed, and
   the value for the material characteristic of the sample using a relationship between the depth of indentation and the test force loaded on the indenter, and
the determiner further calculates a mechanical workload generated during indentation based on the measurement data, accumulates the calculated mechanical workload for each hardness value, and determines the time to replace the indenter based on the accumulated mechanical workload for each hardness value.

3. The hardness tester according to claim 1, further comprising, as a configuration when the processor executes the instruction stored in the memory:
   a display controller that causes a display to display a warning to prompt replacement of the indenter when the determiner determines that the indenter needs to be replaced.

4. The hardness tester according to claim 2, further comprising, as a configuration when the processor executes the instruction stored in the memory:
   a display controller that causes a display to display a warning to prompt replacement of the indenter when the determiner determines that the indenter needs to be replaced.

5. The hardness tester according to claim 1, wherein:
   when the number of times the value for the material characteristic of the sample is measured exceeds a set value, the determiner determines that the indenter needs to be replaced, and when the number of times the value for the material characteristic of the sample is measured does not exceed the set value, the determiner determines the time to replace the indenter based on the measurement data acquired by the acquirer.

6. The hardness tester according to claim 2, wherein:

when the number of times the value for the material characteristic of the sample is measured exceeds a set value, the determiner determines that the indenter needs to be replaced, and when the number of times the value for the material characteristic of the sample is measured does not exceed the set value, the determiner determines the time to replace the indenter based on the measurement data acquired by the acquirer.

7. The hardness tester according to claim 3, wherein:

when the number of times the value for the material characteristic of the sample is measured exceeds a set value, the determiner determines that the indenter needs to be replaced, and when the number of times the value for the material characteristic of the sample is measured does not exceed the set value, the determiner determines the time to replace the indenter based on the measurement data acquired by the acquirer.

8. The hardness tester according to claim 4, wherein:

when the number of times the value for the material characteristic of the sample is measured exceeds a set value, the determiner determines that the indenter needs to be replaced, and when the number of times the value for the material characteristic of the sample is measured does not exceed the set value, the determiner determines the time to replace the indenter based on the measurement data acquired by the acquirer.

9. A hardness testing method of a hardness tester having a CPU and loading a predetermined test force on an indenter and forming an indentation by pressing the indenter into a surface of a sample, the hardness testing method comprising:

measuring, via the CPU, a value for a material characteristic of the sample in conjunction with formation of an indentation;

acquiring, via the CPU, measurement data associated with the value for the material characteristic of the sample measured in said measuring; and determining, via the CPU, a time to replace of the indenter based on the measurement data acquired in said acquiring measurement data.

\* \* \* \* \*

UNITED STATES PATENT AND TRADEMARK OFFICE
CERTIFICATE OF CORRECTION

PATENT NO. : 10,495,557 B2
APPLICATION NO. : 15/869384
DATED : December 3, 2019
INVENTOR(S) : Tsujii et al.

Page 1 of 1

It is certified that error appears in the above-identified patent and that said Letters Patent is hereby corrected as shown below:

In the Claims

At Column 12, Line 22 (Claim 9, Line 12), please change "replace of the" to -- replace the --.

Signed and Sealed this
Ninth Day of June, 2020

Andrei Iancu
*Director of the United States Patent and Trademark Office*